United States Patent
Omura (10) Patent No.: US 9,892,476 B2
(45) Date of Patent: Feb. 13, 2018

(54) MEDICINE DISPENSING SYSTEM

(71) Applicant: TOSHO, INC., Tokyo (JP)

(72) Inventor: Yoshihito Omura, Tokyo (JP)

(73) Assignee: TOSHO, INC., Tokyo (JP)

( * ) Notice: Subject to any disclaimer, the term of this patent is extended or adjusted under 35 U.S.C. 154(b) by 133 days.

(21) Appl. No.: 14/655,977

(22) PCT Filed: Dec. 28, 2012

(86) PCT No.: PCT/JP2012/084091
§ 371 (c)(1),
(2) Date: Jun. 26, 2015

(87) PCT Pub. No.: WO2014/103017
PCT Pub. Date: Jul. 3, 2014

(65) Prior Publication Data
US 2015/0339793 A1    Nov. 26, 2015

(51) Int. Cl.
*G06Q 50/24* (2012.01)
*G06F 17/30* (2006.01)
(Continued)

(52) U.S. Cl.
CPC ............ *G06Q 50/24* (2013.01); *B65B 5/103* (2013.01); *B65B 61/26* (2013.01);
(Continued)

(58) Field of Classification Search
USPC ........................................................ 700/236
See application file for complete search history.

(56) References Cited

U.S. PATENT DOCUMENTS

| | | | |
|---|---|---|---|
| 2002/0096535 A1* | 7/2002 | Zhang | ..................... B65B 35/08 |
| | | | 221/258 |
| 2006/0058918 A1* | 3/2006 | Handfield | ............. A61J 7/0084 |
| | | | 700/236 |

(Continued)

FOREIGN PATENT DOCUMENTS

| | | |
|---|---|---|
| JP | 06-40401 | 2/1994 |
| JP | 2001-87353 | 4/2001 |

(Continued)

OTHER PUBLICATIONS

European Search Report dated Aug. 22, 2016, 9 pages.
International Search Report dated Mar. 5, 2013, Application No. PCT/JP2012/084091, English translation included, 2 pages.

*Primary Examiner* — Gene O Crawford
*Assistant Examiner* — Stephen L Akridge
(74) *Attorney, Agent, or Firm* — Rankin, Hill & Clark LLP (57) ABSTRACT

A medicine dispensing system capable of reliably managing the lot of medicines and the expiration period of medicines is provided. A dispensation data preparation section includes a lot change determination section and a data changing section. The lot change determination section determines, based on lot information, whether or not the lot of the medicines to be used may be changed while medicine dispensing apparatuses are in operation. The dispensation data preparation section is provided with an expiration period determination section to determine with reference to the unpacking date, rather than the dispensation date, whether or not medicines are effective for use. This reliably prevents medicines that were taken out of the medicine packing container from being provided to patients after a number of days have passed.

8 Claims, 4 Drawing Sheets

(51) Int. Cl.
    *B65B 5/10*         (2006.01)
    *B65B 61/26*      (2006.01)
    *G06Q 10/06*      (2012.01)
    *G06Q 10/08*      (2012.01)

(52) U.S. Cl.
    CPC ....... *G06F 17/30876* (2013.01); *G06Q 10/06* (2013.01); *G06Q 10/087* (2013.01)

(56) References Cited

U.S. PATENT DOCUMENTS

| | | | |
|---|---|---|---|
| 2008/0283549 A1* | 11/2008 | Dummer | G07F 11/44 221/174 |
| 2012/0239188 A1* | 9/2012 | Sugimoto | B65B 9/067 700/235 |

FOREIGN PATENT DOCUMENTS

| | | |
|---|---|---|
| JP | 2007-209600 | 8/2007 |
| JP | 2009-070304 | 4/2009 |
| JP | 2012-187273 | 10/2012 |
| WO | 2011/052766 | 5/2011 |

\* cited by examiner

MEDICINE DISPENSING SYSTEM

TECHNICAL FIELD

The present invention relates to a medicine dispensing system.

BACKGROUND ART

JP 2009-70304 A (Patent Document 1) discloses a system having a function of preparing a plurality of dispensation data needed for a medicine dispensing apparatus to perform dispensation based on a multiplicity of prescription data input from a prescription database.

RELATED-ART DOCUMENT

Patent Document

Patent Document 1: JP 2009-70304 A

SUMMARY OF INVENTION

Technical Problem

Although the conventional system can prepare dispensation data needed for a medicine dispensing apparatus to perform dispensation based on a prescription database, the conventional system does not manage the lot of medicines or the expiration period of medicines. Therefore, if a medicine manufacturer recalls medicines, the medicines from the lot being recalled cannot be tracked. Another problem is that the medicines, of which the expiration period is reached after the medicines have been taken out of the medicine packing container and before the number of days of prescription has not passed, are used in dispensation.

An object of the present invention is to provide a medicine dispensing system capable of reliably managing one or both of the lot of medicines and the expiration period of medicines.

Solution to Problem

The present invention provides a medicine dispensing system including a plurality of medicine dispensing apparatuses (17A to 17C), a work instruction data preparation section (9), one or more medicine distribution devices (15), a medicine stock management database (7), a medicine database (5), and a dispensation data preparation section (13).

The plurality of medicine dispensing apparatuses (17A to 17C) each have a function of feeding a set of one or more types of medicines into a packing material based on each of a plurality of dispensation data (DA1 to DA3), and each include a personal medicine distributor (18A to 18C). Each personal medicine distributor (18A to 18C) includes a personal medicine cassette (31) having a plurality of cells (32) for containing one or more types of medicines, and is configured to add the one or more types of medicines, which have been fed into the plurality of cells (32) of the personal medicine cassette (31), to the set of one or more types of medicines to be dispensed based on the dispensation data.

The work instruction data preparation section (9) prepares work instruction data required to take one or more types of medicines, which need to be replenished while the plurality of medicine dispensing apparatuses are in operation, out of one or more types of medicine packing containers and feeds the one or more types of medicines into one or more spare storage containers when it is assumed that the plurality of medicine dispensing apparatuses operate to dispense the medicines based on the plurality of dispensation data (DA1 to DA3). Herein, the term "spare storage containers" refers to storage containers into which medicines have been fed in advance for the purpose of use by the medicine dispensing apparatuses. The spare storage containers may be the same as storage containers to be used by the medicine dispensing apparatuses. In this case, the spare storage containers are directly set to the medicine dispensing apparatuses for replacement. The spare storage containers may be transfer containers provided for the purpose of transfer. In this case, the medicines may be fed from the spare storage containers into the storage containers to be used by the medicine dispensing apparatuses. The term "medicine packing containers" refers to containers configured to store medicines provided by medicine manufacturers, which may be containers such as bottles for individual packing or PTP sheets for PTP packing. If the work instruction data include an instruction to feed a quantity of medicines into the storage containers, the quantity being determined in advance according to the type of the medicines, inventory management can be performed with reference to the number of filled storage containers, which facilitates inventory management. The work instruction data preparation section (9) may prepare work instruction data on an instruction to preferentially prepare medicines that are to be out of stock soon and medicines that are used in a large quantity. This reduces the possibility that medicines are out of stock.

The one or more medicine distribution devices (15) feed the one or more types of medicines into the plurality of cells of the personal medicine cassette based on each of a plurality of distribution data (DB). The medicine stock management database (7) is used to manage the quantity of medicines left in stock in the plurality of medicine dispensing apparatuses (17A to 17C) and the one or more medicine distribution devices (15) and the quantity of medicines left in stock in the one or more filled spare storage containers that have been prepared based on the work instruction data. The medicine database stores various types of medicine information including lot information on the plurality of types of medicines to be dispensed by the plurality of medicine dispensing apparatuses and the number of days for effective use after the respective medicines are taken out of the medicine packing containers.

In the present invention, the dispensation data preparation section (13) includes a main process data preparation section (19) configured to prepare, for each of the plurality of medicine dispensing apparatuses, the plurality of dispensation data needed for the plurality of medicine dispensing apparatuses to separately perform dispensation based on a multiplicity of prescription data input from a prescription database, medicine information data input from the medicine database, and medicine stock information input from the medicine stock management database. The dispensation data preparation section (13) also includes a lot change determination section and a data changing section (25). The lot change determination section determines, based on the lot information, whether or not the lot of the medicines to be used may be changed while the medicine dispensing apparatuses (17A to 17C) are in operation. Herein, the phrase "while the medicine dispensing apparatuses (17A to 17C) are in operation" means "while the medicine dispensing apparatuses (17A to 17C) are performing dispensation based on the dispensation data. The data changing section (25) provides the main process data preparation section (19) with an instruction to change the dispensation data so as to include data on an instruction to change a combination of the plurality of dispensation data prepared for each of the plurality of medicine dispensing apparatuses, when the lot change determination section determines that there is a possibility that the lot of the medicines may be changed while the medicine dispensing apparatuses are in operation, such that there is not a change in the lot while the plurality of medicine dispensing apparatuses (17A to 17C) are in operation. The data changing section (25) provides the main process data preparation section (19) with an instruction to change the dispensation data so as to include data on an instruction to discard the medicines that are relevant to a change in the lot and are left in the medicine dispensing apparatus (17A to 17C) that is relevant to the change in the lot of the medicines, and to use medicines in a new lot when it is determined that there is a possibility that the lot of the medicines to be used is changed while the medicine dispensing apparatuses (17A to 17C) are in operation even if the combination of the plurality of dispensation data is changed. The dispensation data preparation section (13) further includes a distribution data preparation section (21) configured to prepare the plurality of distribution data (DB) for the one or more medicine distribution devices (15) along with the plurality of dispensation data for the medicine dispensing apparatuses each including the personal medicine distributor.

Since the dispensation data preparation section (13) includes the lot change determination section and the data changing section, the lot of the medicines to be used is not changed while the medicine dispensing apparatuses (17A to 17C) are in operation. As a result, according to the present invention, it is possible to prevent a change in the lot of medicines of the same type to be provided to one patient, which makes it possible to manage the lot of medicines reliably compared to the related art.

The work instruction data preparation section (9) discussed above has a function of recording data on an unpacking date, on which the medicine is taken out of the medicine packing container, in the medicine stock management database. The dispensation data preparation section (13) further includes an expiration period determination section (27) configured to determine a dispensation date, on which each of the one or more types of medicines left in stock should be dispensed, and to determine whether or not a first expiration date is later than a second expiration date. The first expiration date is defined by adding to the dispensation date a reference number of days that is determined based on the number of days of prescription included in the prescription data and that is equal to or more than the number of days of prescription. The second expiration date is defined by adding the number of days for effective use to the unpacking date. The expiration period determination section (27) has a function of changing the combination of the plurality of dispensation data prepared for each of the plurality of medicine dispensing apparatuses, when it is determined that the first expiration date is later than the second expiration date, such that there is no combination for which the first expiration date is later than the second expiration date for any of the one or more types of medicines to be dispensed by the plurality of medicine dispensing apparatuses (17A to 17C), and deciding to discard the medicines when there is any combination of the plurality of dispensation data for which the first expiration date is later than the second expiration date for the one or more types of medicines to be dispensed by the plurality of medicine dispensing apparatuses (17A to 17C) even if the combination has been changed, and also has a function of providing the main process data preparation section (19) with an instruction to include, in the dispensation data, data on an instruction to change the combination of the plurality of dispensation data and data on an instruction to discard the medicines decided to be discarded and use new medicines.

Since the dispensation data preparation section (13) is provided with the expiration period determination section (27), it is possible to determine with reference to the unpacking date, rather than the dispensation date, whether or not the medicines are effective for use. This reliably prevents medicines that were taken out of the medicine packing container from being provided to patients after a number of days have passed.

The reference number of days discussed above is preferably determined to be the same as the largest number among a plurality of numbers of days of prescription included in the plurality of prescription data. This allows the expiration period of medicines to be managed well in practice even if the medicines have various numbers of days of prescription. The reference number of days may be variable. This allows application of the present invention also to medicines with different numbers of days for effective use.

If the actual number of days of prescription is to be considered at all times, the reference number of days may be the same as the number of days of prescription included in the prescription data.

As a matter of course, the present invention may also be applied to a case where the medicine dispensing apparatuses do not each include a personal medicine distributor. In this case, it is not necessary to provide the dispensation data preparation section with a distribution data preparation section, and the medicine distribution devices may not be provided.

As a matter of course, the present invention may also be applied to a case where one of the lot of medicines and the expiration period of medicines is managed. If only the lot of medicines is managed, the dispensation data preparation section may not be provided with an expiration period determination section. If only the expiration period of medicines is managed, the dispensation data preparation section may not be provided with a lot change determination section and a data changing section.

DESCRIPTION OF EMBODIMENTS

Figure 1:
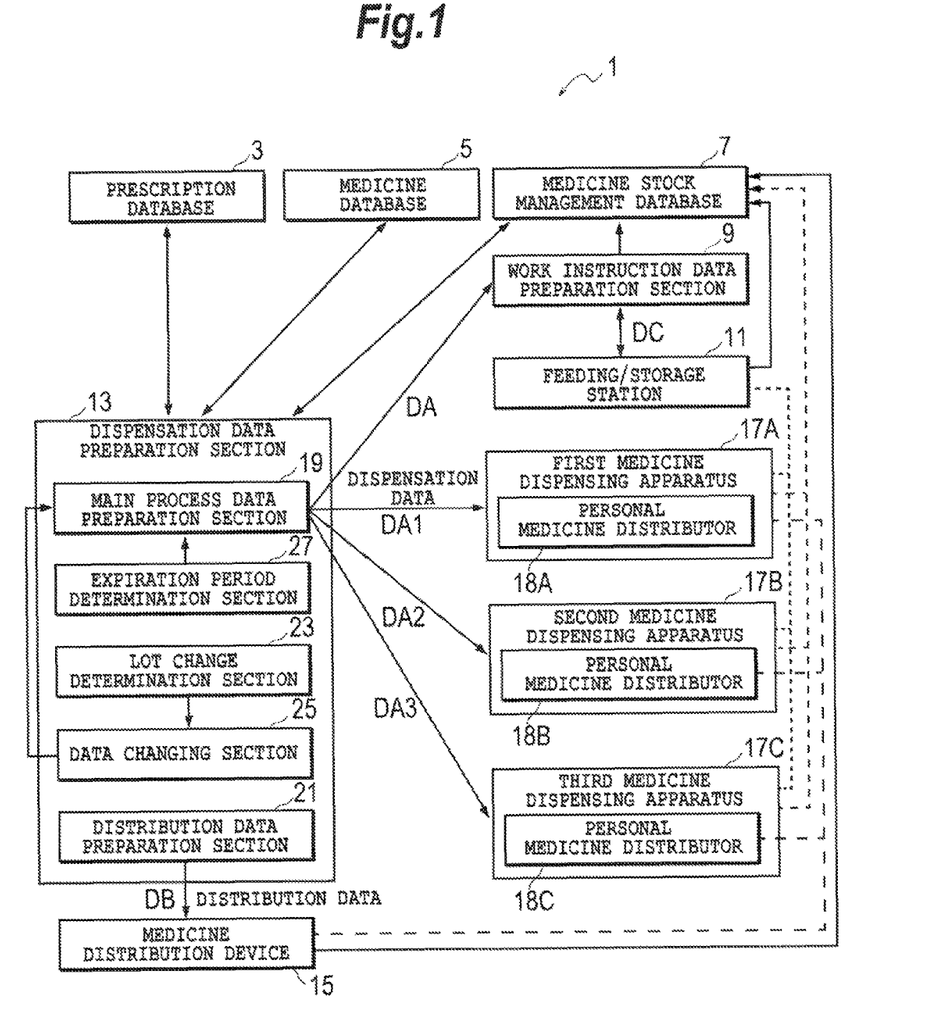
FIG. 1 is a block diagram illustrating an example of the configuration of a medicine dispensing system according to an embodiment of the present invention.

A medicine dispensing system according to an embodiment of the present invention will be described in detail below with reference to the drawings. FIG. 1 is a block diagram illustrating the configuration of a medicine dispensing system 1 according to the embodiment. The medicine dispensing system 1 includes a prescription database 3 that stores prescriptions, a medicine database 5, and a medicine stock management database 7. In order to dispense medicines, the medicine dispensing system 1 additionally includes a work instruction data preparation section 9, a feeding/storage station 11, a dispensation data preparation section 13, one or more medicine distribution devices 15 (one medicine distribution device 15 is illustrated in FIG. 1), and a plurality of medicine dispensing apparatuses 17A to 17C (three medicine dispensing apparatuses are illustrated in FIG. 1 as a typical example). The dispensation data preparation section 13 includes a main process data preparation section 19, a distribution data preparation section 21, a lot change determination section 23, a data changing section 25, and an expiration period determination section 27.

In the embodiment, before the medicine dispensing apparatuses 17A to 17C start operation, the dispensation data preparation section 13 starts preparing dispensation data DA1 to DA3 when prescription data DD are input from the prescription database 3. In the dispensation data preparation section 13, prior to the preparing dispensation data, the lot change determination section 23 determines whether or not there is a possibility that the lot of the medicines may be changed while the medicine dispensing apparatuses 17A to 17C are in operation. The expiration period determination section 27 determines the expiration period of the medicines to be used. When the main process data preparation section 19 of the dispensation data preparation section 13 finally prepares dispensation data, the distribution data preparation section 21 of the dispensation data preparation section 13 prepares distribution data DB to be used by the medicine distribution devices 15. The work instruction data preparation section 9 prepares work instruction data DC required to take one or more types of medicines, which need to be replenished while the plurality of medicine dispensing apparatuses 17A to 17C are in operation, out of one or more types of medicine packing containers and feeds the one or more types of medicines into one or more spare storage containers when it is assumed that the plurality of medicine dispensing apparatuses 17A to 17C operate to dispense the medicines based on the plurality of dispensation data DA (DA1 to DA3) prepared by the main process data preparation section 19. In the feeding/storage station 11, a worker feeds medicines needed for dispensation into storage containers for replacement to store the storage containers based on the work instruction data, for example. The medicine distribution device 15 distributes personal medicines to a plurality of cells 32 of personal medicine cassettes 31 to be used by personal medicine distributors 18A to 18C based on the distribution data DB. Before the medicine dispensing apparatuses 17A to 17C start operation, the worker transfers storage containers that need to be replenished from the feeding/storage station 11 to set the storage containers to the medicine dispensing apparatuses 17A to 17C, and transfers the personal medicine cassettes 31 from the medicine distribution devices 15 to set the personal medicine cassettes 31 to the personal medicine distributors 18A to 18C. After that, the medicine dispensing apparatuses 17A to 17C perform dispensation based on the dispensation data DA1 to DA3, and the personal medicine distributors 18A to 18C of the medicine dispensing apparatuses 17A to 17C put the personal medicines into the medicines to be dispensed in synchronization with the dispensation.

Figure 2:
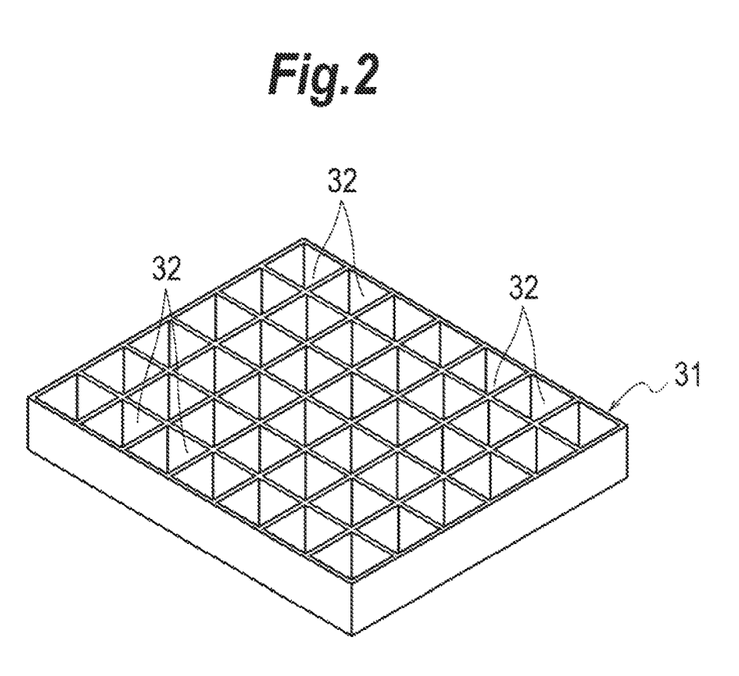
FIG. 2 illustrates an example of a personal medicine cassette.

The function and the operation of the components will be specifically described below. A plurality of types of medicines are contained in a plurality of storage containers. The medicine dispensing apparatuses 17A to 17C have a function of discharging one or more types of medicines from the storage containers and feeding the one or more types of medicines into a packing material based on each of the plurality of dispensation data DA (DA1, DA2, DA3) output from the dispensation data preparation section 13. The medicine dispensing apparatuses 17A to 17C used in the embodiment each include a personal medicine distributor configured to add the one or more types of medicines, which have been fed into the plurality of cells 32 of the personal medicine cassette 31 for containing one or more types of medicines as illustrated in FIG. 2, to the set of medicines to be dispensed based on the dispensation data (DA1, DA2, DA3). Such medicine dispensing apparatuses each including the storage container and the personal medicine distributor 18A to 18C are described in JP 06-40401 A and JP 2001-87353 A, and thus are not described in detail.

The one or more medicine distribution devices 15 feed medicines into the plurality of cells 32 of the personal medicine cassette 31 based on the plurality of distribution data DB prepared by the distribution data preparation section 21 to be discussed later. The medicine distribution devices are not limited to those which feed medicines into a plurality of cells of a personal medicine cassette by the medium of manual work (JP 2007-209600 A, for example), and may be those which automatically feed medicines into a plurality of cells of a personal medicine cassette (JP 2012-187273 A).

The work instruction data preparation section 9 prepares work instruction data DC required to feed a plurality of types of medicines to be used by the plurality of medicine dispensing apparatuses 17A to 17C into the storage containers based on the plurality of dispensation data (DA1, DA2, DA3) prepared by the main process data preparation section 19 of the dispensation data preparation section 13. In the embodiment, the work instruction data preparation section 9 is configured to prepare work instruction data on an instruction to preferentially prepare medicines that are to be out of stock soon and medicines that are used in a large quantity. This reduces the possibility that medicines are out of stock.

The storage containers are used to transfer medicines to the medicine dispensing apparatuses 17A to 17C. Medicines of the same type are fed into one storage container. Normally, a plurality of spare storage containers filled with medicines are prepared for each type of medicines. The medicines can be dispensed, and may be tablets, in capsules, or the like. The worker unseals a medicine packing container that contains designated medicines, and feeds the medicines into spare storage containers that can be used by the medicine dispensing apparatuses 17A to 17C. In the embodiment, the work instruction data preparation section 9 has a function of recording data on an unpacking date d1, on which the medicine is taken out of the medicine packing container, in the medicine stock management database 7. The medicines are fed into the storage containers at the feeding/storage station 11 and the spare storage containers filled with the medicines are stored in the feeding/storage station 11. The medicines are fed by the worker using a feeder or the like. The spare storage containers filled with the medicines are stored in a predetermined storage shelf. In the embodiment, the work instruction data DC include an instruction to feed a quantity of medicines into the spare storage containers, the quantity being determined in advance according to the type of the medicines. As a result, inventory management can be performed with reference to the number of filled spare storage containers, which facilitates inventory management.

The medicine database 5 stores various types of medicine information including lot information on the plurality of types of medicines to be dispensed by the plurality of medicine dispensing apparatuses 17A to 17C and the number of days for effective use after the respective medicines are taken out of the medicine packing containers.

The medicine stock management database 7 is used to manage the quantity of medicines left in stock in the plurality of medicine dispensing apparatuses 17A to 17C and the one or more medicine distribution devices 15 and the quantity of medicines left in stock in the spare storage containers left in the feeding/storage station 11 that have been prepared based on the work instruction data prepared by the work instruction data preparation section 9. The medicine stock management database 7 also stores data on the dispensation date along with the inventory information.

The main process data preparation section 19 of the dispensation data preparation section 13 prepares, for each of the plurality of medicine dispensing apparatuses 17A to 17C, the plurality of dispensation data DA (DA1, DA2, DA3) needed for the plurality of medicine dispensing apparatuses 17A to 17C to separately perform dispensation based on a multiplicity of prescription data input from the prescription database 3, the medicine information data input from the medicine database 5, the medicine stock information input from the medicine stock management database 7, an instruction from the data changing section 25, and an instruction from the expiration period determination section 27. The distribution data preparation section 21 of the dispensation data preparation section 13 prepares the plurality of distribution data DB for the medicine distribution devices 15 as the main process data preparation section 19 prepares the plurality of dispensation data DA1, DA2, and DA3 for the medicine dispensing apparatuses 17A to 17C. The distribution data DB are needed for the medicine distribution devices 15 to prepare personal medicine cassettes to be mounted to the personal medicine distributors 18A to 18C.

The lot change determination section 23 of the dispensation data preparation section 13 determines, based on the lot information stored in the medicine database 5, whether or not the lot of the medicines to be used may be changed while the medicine dispensing apparatuses 17A to 17C are in operation. Before the medicine dispensing apparatuses 17A to 17C start operation, the data changing section 25 provides the main process data preparation section 19 with an instruction to change the dispensation data (DA1, DA2, DA3) so as to include data on an instruction to change a combination of the plurality of dispensation data (DA1, DA2, DA3) prepared for each of the plurality of medicine dispensing apparatuses 17A to 17C, such that there is not a change in the lot while the plurality of medicine dispensing apparatuses 17A to 17C are in operation, when the lot change determination section 23 determines that there is a possibility that the lot of the medicines may be changed while the medicine dispensing apparatuses 17A to 17C are in operation. The data changing section 25 also provides the main process data preparation section 19 with an instruction to change the dispensation data (DA1, DA2, DA3) so as to include data on an instruction to discard the medicines that are relevant to a change in the lot and are left in the medicine dispensing apparatus (17A to 17C) that is relevant to the change in the lot of the medicines, and to use medicines in a new lot, when it is determined that there is a possibility that the lot of the medicines to be used may be changed while the medicine dispensing apparatuses 17A to 17C are in operation even if the combination of the plurality of dispensation data (DA1, DA2, DA3) is changed. Since the dispensation data preparation section 13 includes the lot change determination section 23 and the data changing section 25, the lot of the medicines to be used is not changed while the medicine dispensing apparatuses 17A to 17C are in operation. As a result, according to the embodiment, it is possible to prevent a change in the lot of medicines of the same type to be provided to one patient.

The expiration period determination section 27 of the dispensation data preparation section 13 has a function of determining a dispensation date $d2$, on which each of the medicines left in stock should be dispensed, and deciding to discard the medicines when it is determined that a first expiration date $P1$ ($=d2+RP$) is later than a second expiration date $P2$ ($=d1+N$), wherein the first expiration date $P1$ is defined by adding to the dispensation date $d2$ a reference number of days $RP$ that is determined based on the number of days of prescription included in the prescription data and that is equal to or more than the number of days of prescription, and the second expiration date $P2$ is defined by adding the number of days for effective use (N days, N being a natural number) to the unpacking date $d1$, and also has a function of including, in the dispensation data (DA1, DA2, DA3), data on an instruction to discard the medicines decided to be discarded and use new medicines. That is, the expiration period determination section 27 determines whether or not the following relationships are met.

If the first expiration date $P1$ is earlier than the second expiration date $P2$, the medicines can be used.

If the first expiration date $P1$ is later than the second expiration date $P2$, the medicines are to be discarded.

Specific examples based on the 2011 calendar are as follows.

First Expiration Date $P1$: Dispensation Date (December 1)+reference number of days (two weeks)→December 14

Second expiration date $P2$: unpacking date (November 28)+number of days for effective use (20 days)→December 17

If the above relationship is met, the medicines can be used.

First expiration date $P1$: dispensation date (December 1)+reference number of days (three weeks)→December 21

Second expiration date $P2$: unpacking date (November 28)+number of days for effective use (20 days)→December 17

If the above relationship is met, the medicines are "to be discarded (cannot be used)".

In the embodiment, the expiration period determination section 27 has a function of providing the main process data preparation section 19 with an instruction to change the combination of the plurality of dispensation data prepared for each of the plurality of medicine dispensing apparatuses 17A to 17C, when it is determined that the first expiration date $P1$ is later than the second expiration date $P2$, such that there is no combination for which the first expiration date $P1$ is later than the second expiration date $P2$ for any of the medicines to be dispensed by the plurality of medicine dispensing apparatuses 17A to 17C. The expiration period determination section 27 additionally has a function of deciding to discard the medicines for which the first expiration date $P1$ is later than the second expiration date $P2$ when there is any combination of the plurality of dispensation data for which the first expiration date $P1$ is later than the second expiration date $P2$ for the medicines to be dispensed by the plurality of medicine dispensing apparatuses 17A to 17C even if the combination has been changed, and also has a function of providing the main process data preparation section 19 with an instruction to include, in the dispensation data, data on an instruction to change the combination of the plurality of dispensation data and data on an instruction to discard the medicines decided to be discarded and use new medicines.

Since the dispensation data preparation section 13 is provided with the expiration period determination section 27 in this way, it is possible to determine with reference to the unpacking date, rather than the dispensation date, whether or not the medicines are effective for use. This reliably prevents medicines that were taken out of the medicine packing container from being provided to patients after a number of days have passed.

The reference number of days discussed above can be varied. The reference number of days is preferably determined to be the same as the largest number among a plurality of numbers of days of prescription included in the plurality of prescription data. This allows the expiration period of medicines to be managed well in practice even if the medicines have various numbers of days of prescription. If the actual prescription period is to be considered at all times, the reference number of days may be the same as the number of days of prescription included in the prescription data.

By managing both the lot of medicines and the expiration period of medicines as in the embodiment, "the medicines to be out of stock can be specified beforehand, and the quantity of the medicines to be needed can be calculated", and thus "the medicines to be out of stock can be prepared beforehand". This allows medicines to be smoothly replenished in the feeding/storage station 11. This also makes it possible to shorten the operation stop time of the medicine dispensing apparatuses and improve the efficiency of the medicine dispensing apparatuses.

Operation of the embodiment of FIG. 1 will be described. Before the medicine dispensing apparatuses 17A to 17C start operation, the main process data preparation section 19 of the dispensation data preparation section 13 starts preparing dispensation data DA1 to DA3 when prescription data DD are input from the prescription database 3. In the dispensation data preparation section 13, prior to preparing dispensation data, the lot change determination section 23 determines whether or not there is a possibility that the lot of the medicines may be changed while the medicine dispensing apparatuses 17A to 17C are in operation. The expiration period determination section 27 determines the expiration period of the medicines to be used. When the main process data preparation section 19 of the dispensation data preparation section 13 finally prepares dispensation data, the distribution data preparation section 21 of the dispensation data preparation section 13 prepares distribution data DB to be used by the medicine distribution devices 15. The work instruction data preparation section 9 prepares work instruction data required to feed a plurality of types of medicines to be used by the plurality of medicine dispensing apparatuses 17A to 17C into the storage containers based on the plurality of dispensation data (DA1 to DA3) prepared by the main process data preparation section 19. In the feeding/storage station 11, a worker feeds medicines needed for dispensation into spare storage containers to store the spare storage containers in a storage shelf based on the work instruction data. The medicine distribution device 15 distributes personal medicines to a plurality of cells 32 of personal medicine cassettes 31 to be used by personal medicine distributors 18A to 18C based on the distribution data DB. Before the medicine dispensing apparatuses 17A to 17C start dispensation, the worker transfers from the feeding/storage station 11 spare storage containers for storage containers that need to be replenished indicated in the dispensation data (DA1 to DA3), and sets the spare storage containers to the medicine dispensing apparatuses 17A to 17C. The worker also transfers the personal medicine cassettes 31 from the medicine distribution devices 15 to set the personal medicine cassettes 31 to the personal medicine distributors 18A to 18C of the corresponding medicine dispensing apparatuses 17A to 17C. After the personal medicine cassettes 31 are set, the medicine dispensing apparatuses 17A to 17C perform dispensation based on the dispensation data DA1 to DA3, and the personal medicine distributors 18A to 18C of the medicine dispensing apparatuses 17A to 17C put the personal medicines into the medicines to be dispensed in synchronization with the dispensation.

Figure 3:
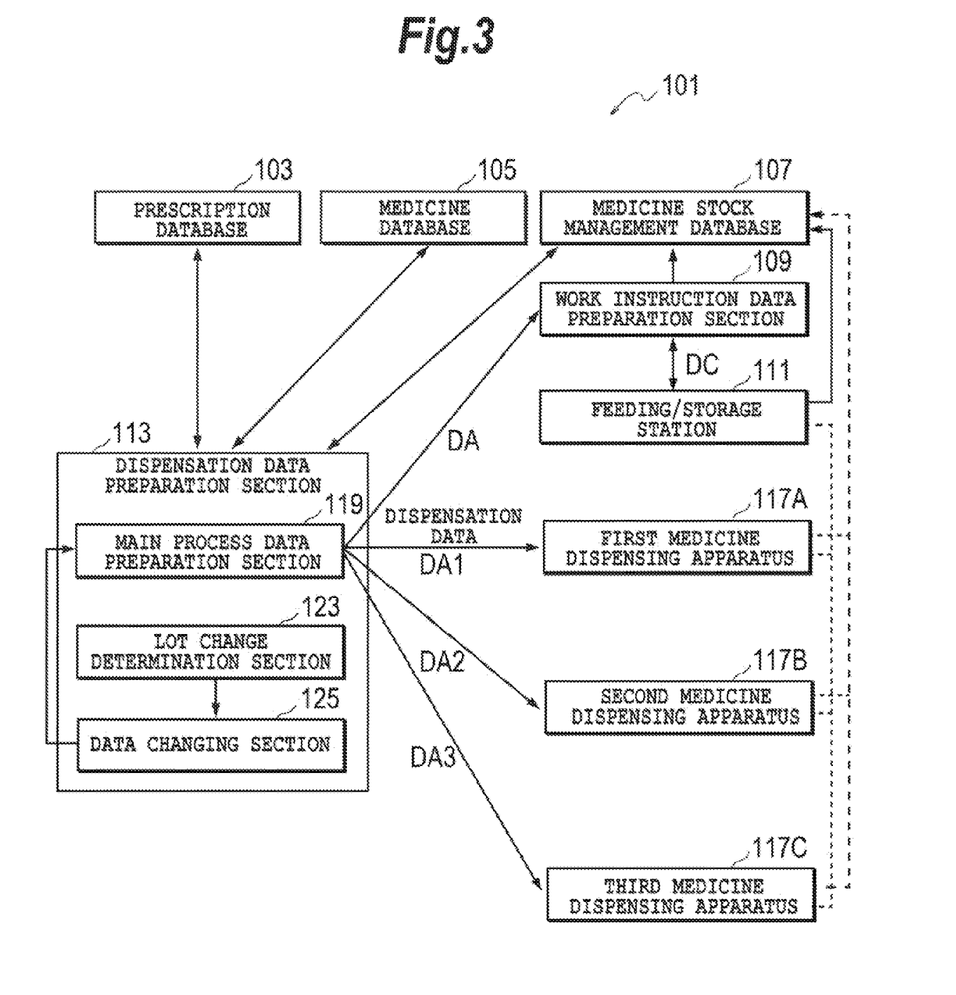
FIG. 3 is a block diagram illustrating an example of the configuration of a medicine dispensing system according to another embodiment of the present invention.

In the embodiment described above, both the lot of medicines and the expiration period of medicines are managed. As a matter of course, however, the present invention may also be applied to a case where one of the lot of medicines and the expiration period of medicines is managed. FIG. 3 is a block diagram illustrating the configuration of a medicine dispensing system 101 according to an embodiment in which only the lot of medicines is managed. In FIG. 3, blocks that are the same as those in the embodiment illustrated in FIG. 1 are denoted by reference numerals obtained by adding 100 to the reference numerals affixed to their counterparts in FIG. 1 to omit their descriptions. The embodiment of FIG. 3 is different from the embodiment of FIG. 1 in that medicine dispensing apparatuses 117A to 117C do not each include a personal medicine distributor, that a dispensation data preparation section 113 is not provided with an expiration period determination section and a distribution data preparation section, and that medicine distribution devices are also not provided. The medicine dispensing system according to the embodiment cannot manage the expiration period, but can be used in countries in which expiration period management is not required.

Figure 4:
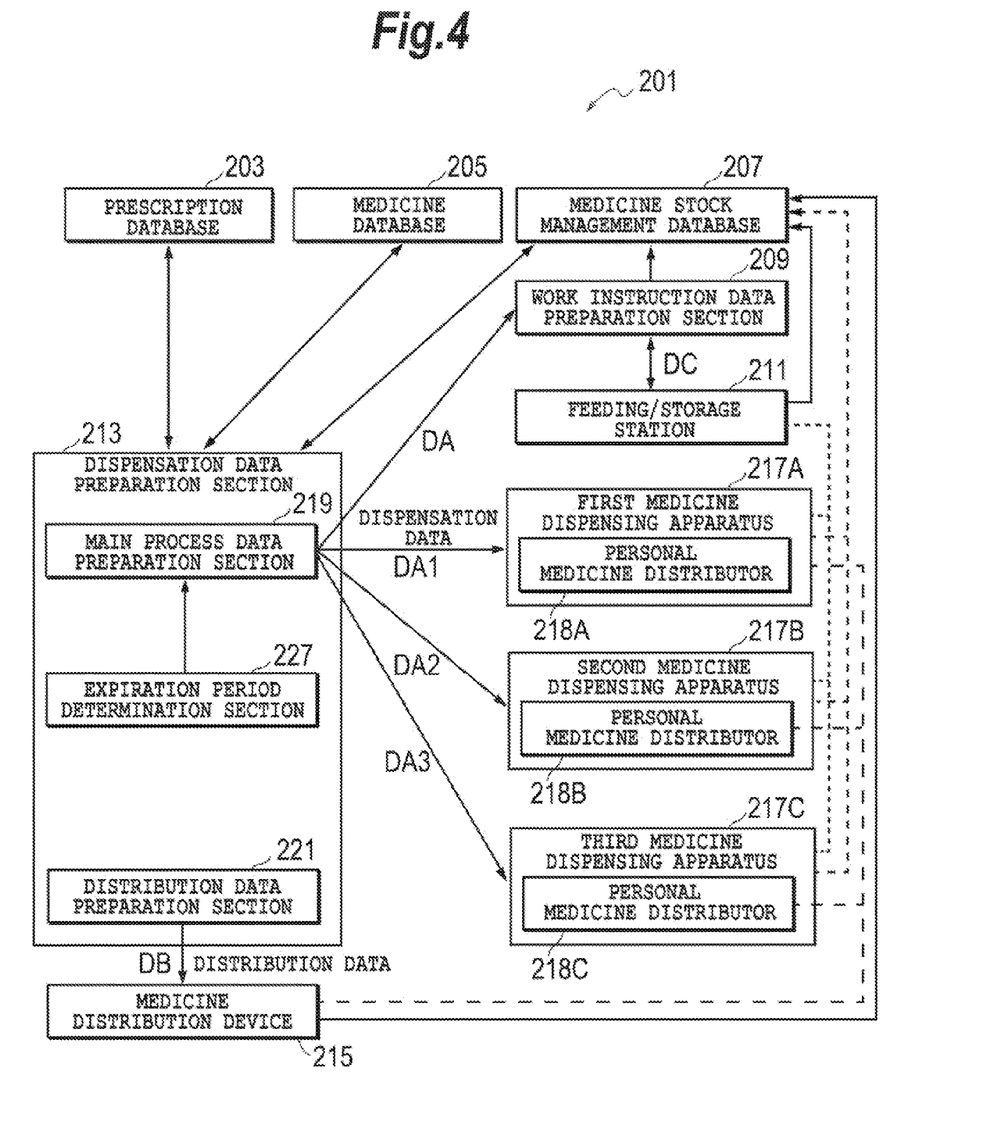
FIG. 4 is a block diagram illustrating an example of the configuration of a medicine dispensing system according to another embodiment of the present invention.

FIG. 4 is a block diagram illustrating the configuration of a medicine dispensing system 201 according to an embodiment in which only the expiration period of medicines is managed. In FIG. 4, blocks that are the same as those in the embodiment illustrated in FIG. 1 are denoted by reference numerals obtained by adding 200 to the reference numerals affixed to their counterparts in FIG. 1 to omit their descriptions. The embodiment of FIG. 4 is different from the embodiment of FIG. 1 in that a dispensation data preparation section 213 is not provided with a lot change determination section and a data changing section. The embodiment can be used in countries in which lot management is not required and only expiration period management is required. In Japan, incidentally, neither lot management nor expiration period management is required by law.

Data processing in each of the embodiments described above is performed by one or more computers or processors.

INDUSTRIAL APPLICABILITY

According to the present invention, it is possible to prevent a change in the lot of medicines of the same type to be provided to one patient, which makes it possible to manage the lot of medicines reliably compared to the related art. According to the present invention, in addition, it is possible to reliably prevent medicines that were taken out of the medicine packing container from being provided to patients after a number of days have passed.

DESCRIPTION OF REFERENCE NUMERALS 1 medicine dispensing system
3 prescription database 5 medicine database
7 medicine stock management database
9 work instruction data preparation section
11 feeding/storage station
13 dispensation data preparation section
15 medicine distribution device
17a to 17c medicine dispensing apparatus
18A to 18C personal medicine distributor
19 main process data preparation section
21 distribution data preparation section
23 lot change determination section
25 data changing section
27 expiration period determination section
31 personal medicine cassette
32 cell

The invention claimed is:

1. A medicine dispensing system comprising:
a plurality of medicine dispensing apparatuses each having a function of feeding a set of one or more types of medicines into a packing material based on each of a plurality of dispensation data;
a work instruction data preparation section configured to prepare work instruction data required to take one or more types of medicines, which need to be replenished while the plurality of medicine dispensing apparatuses are in operation, out of one or more types of medicine packing containers and to feed the one or more types of medicines into one or more spare storage containers when it is assumed that the plurality of medicine dispensing apparatuses operate to dispense the medicines based on the plurality of dispensation data;
a medicine stock management database used to manage the quantity of medicines left in stock in the plurality of medicine dispensing apparatuses and the quantity of medicines left in stock in the one or more spare storage containers that have been prepared based on the work instruction data;
a medicine database configured to store various types of medicine information including lot information on the plurality of types of medicines to be dispensed by the plurality of medicine dispensing apparatuses; and
a dispensation data preparation section comprising:
 a main process data preparation section configured to prepare, for each of the plurality of medicine dispensing apparatuses, the plurality of dispensation data needed for the plurality of medicine dispensing apparatuses to separately perform dispensation based on a multiplicity of prescription data input from a prescription database, medicine information data input from the medicine database, and medicine stock information input from the medicine stock management database;
 a lot change determination section configured to determine, based on the lot information and before the medicine dispensing apparatuses start operation, whether or not there is a possibility that the lot of the medicines to be used may be changed while the medicine dispensing apparatuses are in operation; and
 a data changing section configured to provide the main process data preparation section with an instruction to change the dispensation data so as to include data on an instruction to change a combination of the plurality of dispensation data prepared for each of the plurality of medicine dispensing apparatuses, when the lot change determination section determines that there is a possibility that the lot of the medicines may be changed while the medicine dispensing apparatuses are in operation, such that there is not a change in the lot while the plurality of medicine dispensing apparatuses are in operation, and to change the dispensation data so as to include data on an instruction to discard the medicines that are relevant to a change in the lot and left in the medicine dispensing apparatus that is relevant to the change in the lot of the medicines and use medicines in a new lot when it is determined that the lot of the medicines to be used is changed while the medicine dispensing apparatuses are in operation even if the combination of the plurality of dispensation data is changed.

2. The medicine dispensing system according to claim 1, wherein:
at least one of the plurality of medicine dispensing apparatuses includes a personal medicine distributor configured to add medicines, which have been fed into a plurality of cells of a personal medicine cassette for containing one or more types of medicines, to the set of medicines to be dispensed based on the dispensation data;
the at least one of the plurality of medicine dispensing apparatuses further includes one or more medicine distribution devices configured to feed the one or more types of medicines into the plurality of cells of the personal medicine cassette based on each of a plurality of distribution data; and,
the dispensation data preparation section further comprises a distribution data preparation section configured to prepare a plurality of distribution data for the one or more medicine distribution devices along with the plurality of dispensation data for the medicine dispensing apparatuses each including the personal medicine distributor.

3. The medicine dispensing system according to claim 1, wherein:
the work instruction data preparation section has a function of recording data on an unpacking date, on which the medicine is taken out of the medicine packing container, in the medicine stock management database; and
the dispensation data preparation section further comprises an expiration period determination section having a function of determining a dispensation date, on which each of the one or more types of medicines left in stock should be dispensed, changing the combination of the plurality of dispensation data prepared for each of the plurality of medicine dispensing apparatuses, when it is determined that a first expiration date is later than a second expiration date, such that there is no combination for which the first expiration date is later than the second expiration date for any of the one or more types of medicines to be dispensed by the plurality of medicine dispensing apparatuses, wherein the first expiration date is defined by adding to the dispensation date a reference number of days that is determined based on the number of days of prescription included in the prescription data and that is equal to or more than the number of days of prescription, and the second expiration date is defined by adding the number of days for effective use to the unpacking date, and deciding to discard the medicines for which the first expiration date is later than the second expiration date when there is any combination of the plurality of dispensation data for which the first expiration date is later than the second expiration date for the one or more types of medicines to be dispensed by the plurality of medicine dispensing apparatuses even if the combination has been changed, and also having a function of providing the main process data preparation section with an instruction to include, in the dispensation data, data on an instruction to change the combination of the plurality of dispensation data and data on an instruction to discard the medicines decided to be discarded and use new medicines.

4. The medicine dispensing system according to claim 3, wherein
the reference number of days is determined to be the same as the largest number among a plurality of numbers of days of prescription included in the plurality of prescription data.

5. The medicine dispensing system according to claim 4, wherein
the reference number of days is changeable.

6. The medicine dispensing system according to claim 3, wherein
the reference number of days is the same as the number of days of prescription included in the prescription data.

7. The medicine dispensing system according to claim 1, wherein
the work instruction data preparation section prepares the work instruction data including an instruction to execute the work using medicines in the new lot when the dispensation data including data on an instruction to use medicines in the new lot are input.

8. The medicine dispensing system according to claim 1, wherein
the work instruction data preparation section prepares work instruction data on an instruction to preferentially prepare medicines that are to be out of stock soon and medicines that are used in a large quantity.

* * * * *